(12) United States Patent
Descombes et al.

(10) Patent No.: US 12,308,120 B2
(45) Date of Patent: May 20, 2025

(54) ANALYSIS AND CHARACTERIZATION OF EPITHELIAL TISSUE STRUCTURE

(71) Applicants: Kenvue Brands LLC, Summit, NJ (US); Inria (Institut national de recherche en informatique et en automatique), Les Chesnay-Rocquencourt (FR)

(72) Inventors: Xavier Descombes, Sophia Antipolis (FR); Imane Lboukili, Val de Reuil (FR); Thierry Oddos, Clamart (FR); Georgios N. Stamatas, Val de Reuil (FR)

(73) Assignee: Kenvue Brands LLC/Inria (Institut national de recherche en informatique et en automatique), Summit, NJ (US)

( * ) Notice: Subject to any disclaimer, the term of this patent is extended or adjusted under 35 U.S.C. 154(b) by 417 days.

(21) Appl. No.: 17/943,477

(22) Filed: Sep. 13, 2022

(65) Prior Publication Data

US 2023/0084952 A1 Mar. 16, 2023

Related U.S. Application Data

(60) Provisional application No. 63/244,981, filed on Sep. 16, 2021.

(51) Int. Cl.
*G16H 50/20* (2018.01)
(52) U.S. Cl.
CPC .................................. *G16H 50/20* (2018.01)
(58) Field of Classification Search
None
See application file for complete search history.

(56) References Cited

U.S. PATENT DOCUMENTS

| | | | |
|---|---|---|---|
| 8,649,589 | B2 | 2/2014 | Gareau |
| 2003/0148295 | A1 | 8/2003 | Wan et al. |
| 2007/0038384 | A1 | 2/2007 | Kirk et al. |
| 2007/0238941 | A1 | 10/2007 | Nikolovski et al. |
| 2009/0292027 | A1 | 11/2009 | Ruvolo et al. |
| 2010/0292543 | A1 | 11/2010 | Levitt et al. |
| 2012/0219205 | A1* | 8/2012 | Gareau ............... G06T 7/0014 382/133 |

(Continued)

FOREIGN PATENT DOCUMENTS

EP 3660736 A1 6/2020

OTHER PUBLICATIONS

Chen, Min et al., AI-Skin: Skin disease recognition based on self-learning and wide data collection through a closed-loop framework; Information Fusion; vol. 54, Jun. 7, 2019; pp. 1-9.

(Continued)

*Primary Examiner* — Andrew H Lam
(74) *Attorney, Agent, or Firm* — Samuel J. Gee (57) ABSTRACT

Methods for non-invasive or minimally invasive assessment of epithelial tissue structure are disclosed. Digital imaging and processing are used to identify cell locations. More specifically, an automated algorithm that may be used to identify epithelial tissue structure, and/or to specify the coordinates/locations of cells in the epithelial tissue structure, through non-invasive or minimally invasive imaging, and use of this information to extract values of epithelial structure related parameters are disclosed.

13 Claims, 6 Drawing Sheets

(56) References Cited

U.S. PATENT DOCUMENTS

| | | |
|---|---|---|
| 2019/0209711 A1 | 7/2019 | Bensaci et al. |
| 2020/0167927 A1* | 5/2020 | Ina .................. G16H 20/10 |
| 2020/0360259 A1 | 11/2020 | Capone et al. |

OTHER PUBLICATIONS

Kothari, Arya et al.; Cosmetic Skin Type Classification Using CNN with Product Recommendation; 2021 12th Int'l. Conference on Computing Communication and Networking Technologies; Jul. 6, 2021, pp. 1-6.

International Search Report; PCT/IB2022/058769; Feb. 15, 2023.

Gawkrodger D.J.; Dermatology: An Illustrated Colour Text. Sixth Ed.; Elsevier; Edinburgh, (2017).

Graham-Brown, Robin A. C. and John F. Bourke. "Mosby's color atlas and text of dermatology." (2007). Text Book.

Guillaud, M. et al.; Quantitative histopathological analysis of cervical intra-epithelial neoplasia sections: Methodological issues; Cellular Oncology; 26 (2004) 31-43.

Frangi, A.F. et al.; Multiscale vessel enhancement filtering; In Medical Image Computing and Computer-Assisted Intervention—MICCAI'98, W.M. Wells, A. Colchester and S.L. Delp (Eds.), Lecture Notes in Computer Science, vol. 1496—Springer Verlag, Berlin, Germany, (1998) pp. 130-137.

Jadwiga Rogowska; Overview and Fundamentals of Medical Image Segmentation; Handbook of Medical Image Processing and Analysis; Elsevier Inc. (2008) pp. 73-90.

Bensaci, J, et al.; "Geometrical and topological analysis of confocal microscopy images reveals dynamic maturation of epidermal structures during the first years of life," Journal of Biomedical Optics, vol. 20, No. 9, Sep. 1, 2015, pp. 095004-1 to 095004-5.

Invitation to Pay Additional Fees, Dated Dec. 21, 2022, PCT/IB2022/058769.

Cork MJ (1997) The importance of skin barrier function. Journal of Dermatological Treatment; 8: Suppl 1, S7-S13.

Holden C et al (2002) Advised best practice for the use of emollients in eczema and other dry skin conditions. Journal of Dermatological Treatment; 13: 3, 103-106.

Rudy SJ and Parham-Vetter PC (2003) Percutaneous absorption of topically applied medication. Dermatology Nursing; 15: 2, 145-152.

Gareau, Automated identification of epidermal keratinocytes in reflectance confocal microscopy, Journal of Biomedical Optics, 16(3): Mar. 2011: 030502-1 to 030502-3.

Nehal et al., Skin Imaging with Reflectance Confocal Microscopy, Semin Cutan Med Surg 27:37-43 © 2008 Elsevier Inc.

A. Csikász-Nagy et al., "Cooperation and competition in the dynamics of tissue architecture during homeostasis and tumorigenesis," Semin. Cancer Biol. 23(4), 293-298 (2013).

Martial Guillaud, Calum E. MacAulay, Jean C. Le Riche, Chris Dawe, Jagoda Korbelik, Stephen Lam, "Quantitative architectural analysis of bronchial intraepithelial neoplasia," Proc. SPIE 3921, Optical Diagnostics of Living Cells III, (Apr. 27, 2000) https://doi.org/10.1117/12.384231.

Jiafu Wang, Min Yang, Li Yang, Yun Zhang, Jing Yuan, Qian Liu, Xiaohua Hou, Ling Fu, A Confocal Endoscope for Cellular Imaging, Engineering, vol. 1, Issue 3, 2015, pp. 351-360, ISSN 2095-8099, https://doi.org/10.15302/J-ENG-2015081. (https://www.sciencedirect.com/science/article/pii/S2095809916300121).

P. Márquez-Neila, L. Baumela and L. Alvarez, "A Morphological Approach to Curvature-Based Evolution of Curves and Surfaces," in IEEE Transactions on Pattern Analysis and Machine Intelligence, vol. 36, No. 1, pp. 2-17, Jan. 2014, doi: 10.1109/TPAMI.2013.106).

Wang et al. "Age-related morphological changes of the dermal matrix in human skin documented in vivo by multiphoton microscopy" J. Biomed. Opt. 23(3), 030501 2018.

J. Kamarainen, "Gabor features in image analysis," 2012 3rd International Conference on Image Processing Theory, Tools and Applications (IPTA), 2012, pp. 13-14, doi: 10.1109/IPTA.2012.6469502.

Sato et al., Three-dimensional multi-scale line filter for segmentation and visualization of curvilinear structures in medical images, Medical Image Analysis (1998) vol. 2, No. 2, pp. 143-168.

Stamatas, G., Development of a non-invasive optical method for assessment of skin barrier to external penetration; Biomedical Optics and 3D Imaging OSA (2012) pp. 1-3.

Stamatas, G., Infant Skin Microstructure Assessed In Vivo Differs from Adult Skin in Organization and at the Cellular Level; Pediatric Dermatology; vol. 27, No. 2; pp. 125-131; (2010).

* cited by examiner

WATERSHED WITHOUT
SPATIAL NORMALIZATION

*FIG. 3A*

WATERSHED WITH
SPATIAL NORMALIZATION

*FIG. 3B*

MORPHOLOGICAL SNAKES
WITH SPATIAL NORMALIZATION,
WITHOUT COUNTOUR HIGHLIGHTING
AND NEGATIVE BALLOON

| Method | Parameters | Input | Optimization |
|---|---|---|---|
| Gabor | $\lambda$ – Wavelength of the sinusoidal component, controls the width of the strips of the Gabor function<br>$\sigma$ – The standard deviation of the Gaussian envelope, controls the function's bandwidth/overall size i.e. number of strips.<br>$\gamma$ – The spatial aspect ratio and specifies the ellipticity of the support of Gabor function, controls the height of the strips<br>$\Theta$ – The orientation of the filter<br>Black_ridges = False | Fourier filtered image | Increase length of the filter |
| Frangi to detect blobs | $\gamma$ – Linderberg normalization factor to compare the response of a differential operators at multiples scales, adjust filter's sensitivity to areas of high variance/texture/structure<br>$\sigma$ – Filter's scale<br>$\beta$ – Correwction constant that adjust the filter's sensitivity to deviation from a blob-like structure<br>$\alpha$ – Correction constant that adjust the filter's sensitivity to deviation from a plate-like structure<br>Black_ridges = True | Fourier filtered image negative | Change sigma to detect smaller cells |
| Frangi to detect ridges | Calculates the eigenvectors of the Hessian to compute the similarity of an image region to white vessels (membranes) [Frangi]<br>$\gamma, \sigma, \beta, \alpha$ – Definitions above<br>Black_ridges = False | Fourier filtered image | |
| Sato | Filters an image with the Sato tubeness filter to detect continuous ridges, e.g. tubes, wrinkles, rivers...Calculates the Hessian matrix to compute the similarity of an image region to tubes [Sato]<br>$\sigma$ – Filter's scale<br>Black_ridges = False | Original image | |

*FIG. 5*

ANALYSIS AND CHARACTERIZATION OF EPITHELIAL TISSUE STRUCTURE

CROSS-RELATED APPLICATION

The present application claims the benefit of the earlier filing date of U.S. provisional patent application 63/244,981, filed Sep. 16, 2021, the entirety of which application is hereby incorporated by reference herein as if fully set forth herein.

TECHNICAL FIELD

The invention relates to use of imaging technologies to analyze and characterize epithelial tissue structure in a non-invasive or minimally invasive manner.

BACKGROUND

Figure 1A:
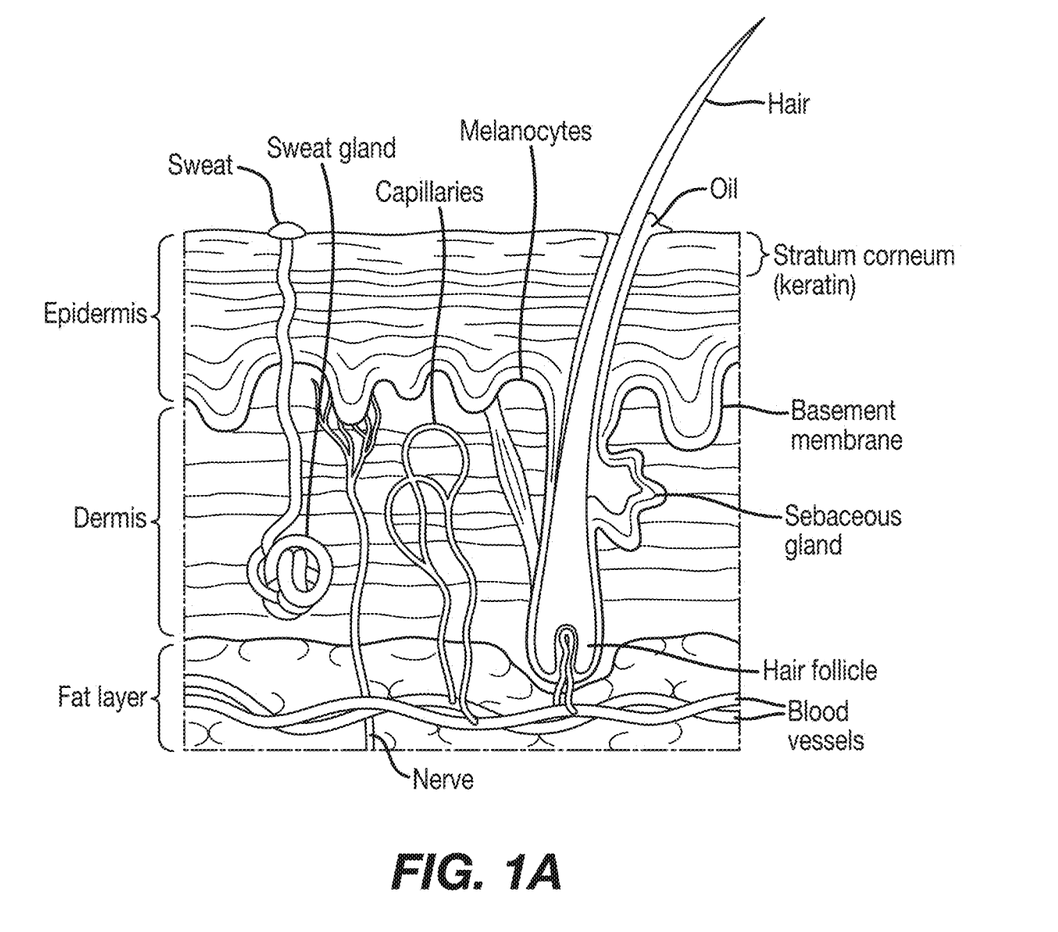
FIGS. 1a and 1b illustrate layers of the skin.
Figure 1B:
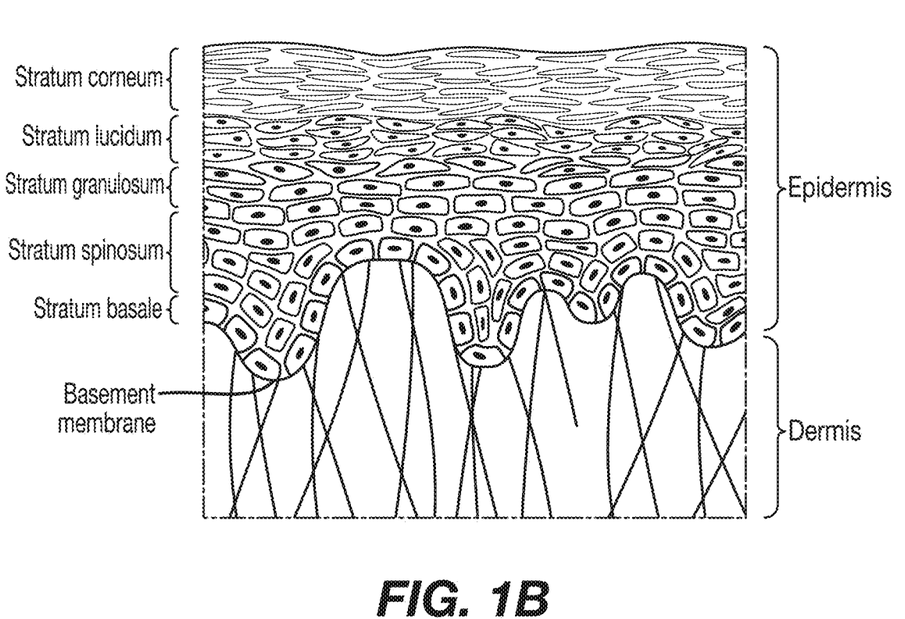

Skin is a complex, multi-layered and dynamic system that provides a protective covering defining the interactive boundary between an organism and the environment. It is the largest organ of the body and is vitally important to our health. Skin comprises three principal layers, the epidermis, the basement membrane also known as the dermis and a layer of subcutaneous fat also known as the hypodermis, as shown in FIG. 1a and FIG. 1b, which are each taken from Lawton S (2019) Skin 1: the structure and functions of the skin, Nursing Times [online]; 115, 12, 30-33.

The dermis provides the epidermis with mechanical support. It is also its nurturing element. It consists mainly of fibroblasts and an extracellular matrix composed mainly of collagen and elastin.

The epidermis is in contact with the external environment. Its role is to protect the body from dehydration and external aggression, whether chemical, mechanical, physical or infectious.

The epidermis primarily comprises keratinocytes in progressive stages of differentiation. Keratinocytes produce the protein keratin and are the major building blocks (cells) of the epidermis. As the epidermis is avascular (contains no blood vessels), it is entirely dependent on the underlying dermis for nutrient delivery and waste disposal through the basement membrane.

The prime function of the epidermis is to act as a physical and biological barrier to the external environment, preventing penetration by irritants and allergens. At the same time, it prevents the loss of water and maintains internal homeostasis. (Gawkrodger D J (2007) Dermatology: An Illustrated Colour Text. Edinburgh: Churchill Livingstone; Cork M J (1997) The importance of skin barrier function. Journal of Dermatological Treatment; 8: Suppl 1, S7-S13). The epidermis is composed of layers; most body parts have four layers, but those with the thickest skin have five. The layers are:
  stratum corneum;
  stratum lucidum (only found in thick skin—that is, the palms of the hands, the soles of the feet and the digits);
  stratum granulosum;
  stratum spinosum; and
  stratum basale.

The epidermis also contains other cell structures. Keratinocytes make up around 95% of the epidermal cell population—the others being melanocytes, Langerhans cells, resident T lymphocytes and Merkel cells.

Figure 2:
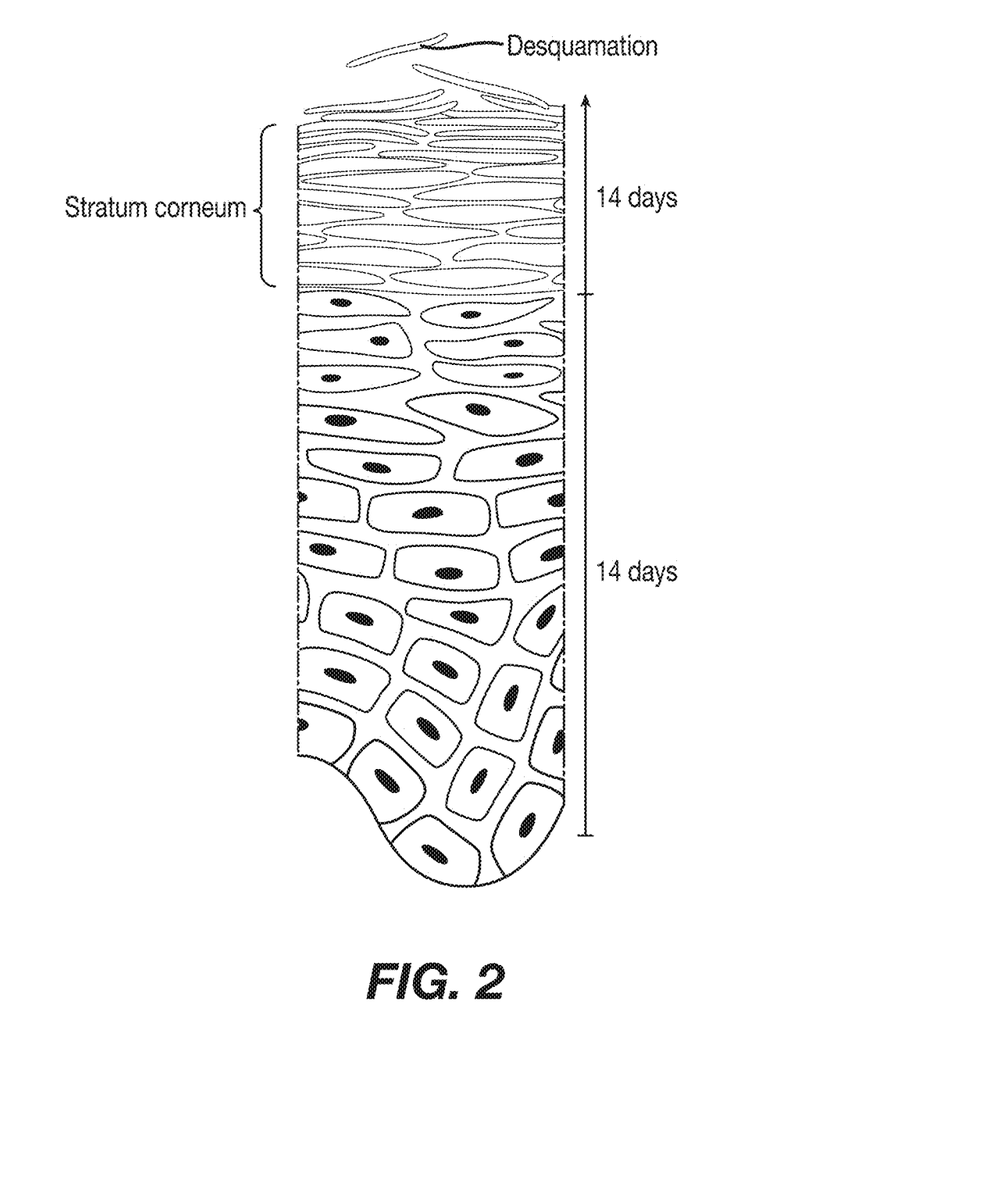
FIG. 2 illustrates desquamation.
Figure 3A:
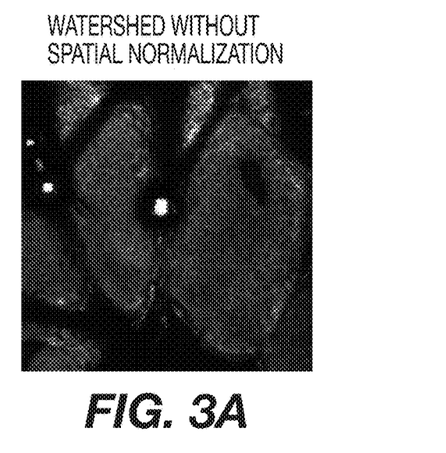
FIG. 3a shows watershed without normalization.
Figure 3B:
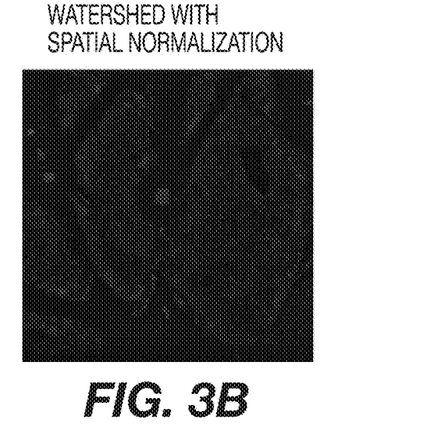
FIG. 3b shows watershed with spatial normalization.
Figure 3C:
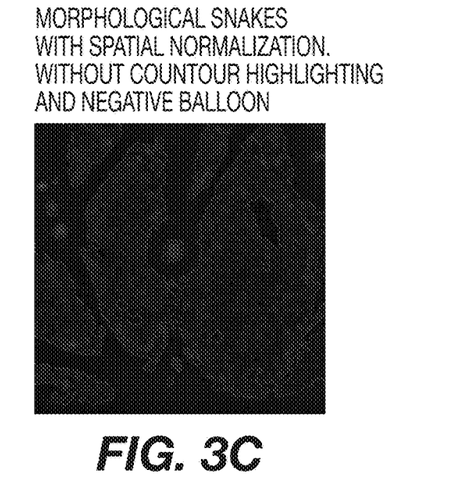
FIG. 3c shows morphological snakes with spatial normalization without contour and negative balloon.
Figure 4:
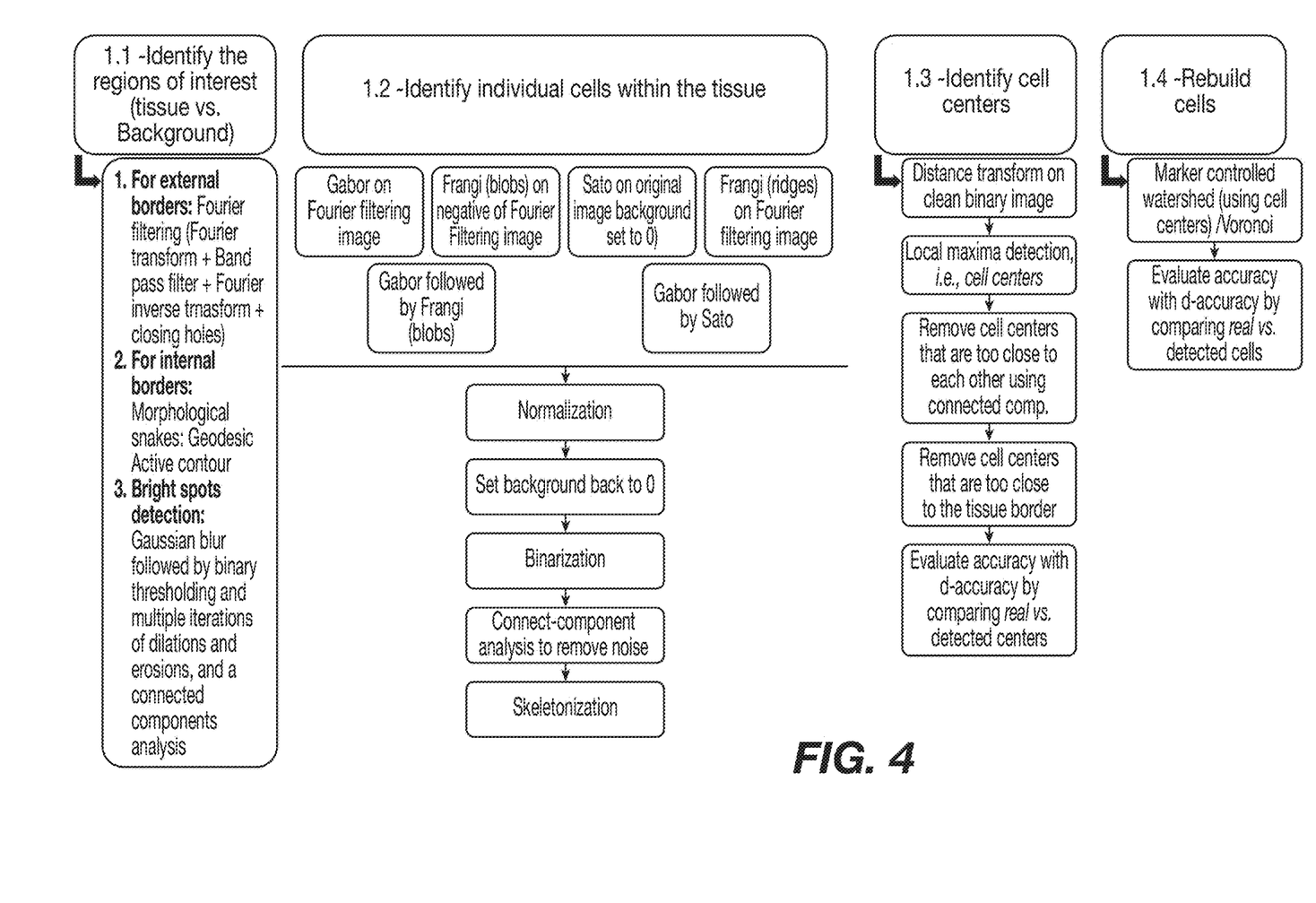
FIG. 4 illustrates the work flow for automated cell identification.

Keratinocytes are formed by division in the stratum basale. As they move up through the stratum spinosum and stratum granulosum, they differentiate to form a rigid internal structure of keratin, microfilaments and microtubules (keratinization). The outer layer of the epidermis, the stratum corneum, is composed of layers of flattened dead cells (corneocytes) that have lost their nucleus. These cells are then shed from the skin (desquamation); this complete process takes approximately 28 days. (See FIG. 2).

Between the corneocytes there is a complex mixture of lipids and proteins (Cork, 1997); these intercellular lipids are processed by enzymes from keratinocytes to produce a lipid mixture of ceramides (phospholipids), fatty acids and cholesterol. These molecules are arranged in a highly organized fashion, fusing with each other and the corneocytes to form the skin's lipid barrier against water loss and penetration by allergens and irritants. (Holden C et al (2002) Advised best practice for the use of emollients in eczema and other dry skin conditions. Journal of Dermatological Treatment; 13: 3, 103-110).

The stratum corneum can be visualized as a brick wall, with the corneocytes forming the bricks and lamellar lipids forming the mortar. As corneocytes contain water-retaining substances collectively referred to as natural moisturizing factors, they attract and hold onto water. The water content of the corneocytes controls their pliability and elasticity, preventing the formation of fissures and cracks (Holden et al, 2002; Cork, 1997).

The highly organized structure of the stratum corneum regulates the amount and rate of percutaneous absorption. (Rudy S J and Parham-Vetter P C (2003) Percutaneous absorption of topically applied medication. Dermatology Nursing; 15: 2, 145-152). One of the most important factors affecting this is skin hydration and environmental humidity.

Melanocytes are found in the stratum basale and are scattered among the keratinocytes along the basement membrane. They produce the pigment melanin, manufactured from tyrosine, which is an amino acid, packaged into cellular vesicles called melanosomes, and transported and delivered into the cytoplasm of the keratinocytes (Graham-Brown and Bourke, 2006). The main function of melanin is to absorb ultraviolet (UV) radiation to protect against its harmful effects.

The pattern of keratinocyte organization is important in distinguishing between diseased/damaged and normal skin. Thus, keratinocyte organization may be a target for cosmetic skin products.

U.S. Published Application No. 20030148295 to Wan et al. discloses methods of using gene expression profiles, including epithelial gene expression profiles, to confirm tissue or cell identification.

U.S. Published Application No. 20070038384 to Kirk et al. discloses devices and methods for patterning cells in a predetermined array for subsequent observation and measurement of cell motility and associated treatment options.

U.S. Published Application No. 20100292543 to Levitt et al. discloses methods and computer program products for analyzing tissue. The tissue is exposed to light at the appropriate wavelengths for inducing fluorescence. Images of the fluorescing tissue are taken at two or more depths within the tissue. The power spectral density (PSD) function is determined for each image at a different depth within the tissue. A characteristic of each PSD function determined is compared, and it is determined whether or not the tissue exhibits a pre-cancerous characteristic.

U.S. Pat. No. 8,649,589 to Oregon Health and Science University and Gareau, Automated identification of epidermal keratinocytes in reflectance confocal microscopy, Journal of Biomedical Optics, 16(3): March 2011: 030502-1 to 030502-3, disclose an algorithm that can be used to identify keratinocytes through confocal imaging. U.S. Pat. No. 8,649,589 discloses that since organelles and intercellular tissue constituents are comparably sized to the illumination wavelength and are of high refractive index relative to the surrounding medium, they provide bright contrast to the nuclei in keratinocytes.

U.S. Published Application No. 20070238941 to Johnson & Johnson Consumer Inc. discloses a method of evaluating skin comprising the steps of introducing a fluid comprising water to the skin; measuring at least one skin barrier property that correlates to the water content of the skin over time, the measuring step comprising taking at least one measurement of the skin barrier property in the time frame starting from completion of the introducing step up to about 60 seconds after such completion of the introducing step and optionally taking a plurality of skin barrier property measurements after about 60 seconds after completion of the introducing step; and comparing the skin water content measurements of the measuring step with at least one Comparative Data Set to determine the relative infant-like barrier properties of the skin. The reference discloses that the measuring step comprises measuring one or more property of the skin selected from the group consisting of conductance, capacitance, impedance, FTIR, NIR, Raman Confocal, and combinations of two or more thereof.

U.S. Application No. 20190209711 to Johnson & Johnson Consumer Inc. discloses method of evaluating a potential impact of a surfactant system on infant skin, comprising: a) topically applying said surfactant system to adult skin; b) topically applying a marker to said surfactant system treated adult skin; c) measuring penetration of said marker into said surfactant system treated adult skin; d) using a computational model of adult skin penetration to visualize penetration of the marker by optimizing penetration parameters so that the model of adult skin penetration profiles match the experimental data; e) transferring the optimized penetration parameters to a computational model of infant skin; and f) determining the penetration of the marker in the computational model of infant skin. The reference discloses that confocal Raman micro-spectroscopy may be used to follow the concentration profile of the marker through the skin.

Nehal et al., Skin Imaging With Reflectance Confocal Microscopy, Semin Cutan Med Surg 27:37-43 ©2008 Elsevier Inc, discloses basic principles of skin imaging with reflectance confocal microscopy.

Stamatas et al., Development of a non-invasive optical method for assessment of skin barrier to external penetration, Biomedical Optics and 3D Imaging OSA (2012), discloses the use of characteristic Raman spectrum of caffeine to track caffeine penetration through adult skin to demonstrate the impact of (1) sodium lauryl sulfate and (2) barrier cream on stratum corneum barrier function.

Stamatas et al. discloses that the epidermis organization in babies is different compared to adult: Stamatas et al. Pediatr Dermatol 27(2), 125-131, 2010.

Benasci et al. discloses measuring topological features from confocal images: Bensaci et al. J Biomed Optics 20(9), 095004, 2015.

A. Csikasz-Nagy et al. discloses that epidermal topology is altered in disease: A. Csikász-Nagy et al., "Cooperation and competition in the dynamics of tissue architecture during homeostasis and tumorigenesis," Semin. Cancer Biol. 23(4), 293-298 (2013). See also, Martial Guillaud, Calum E. MacAulay, Jean C. Le Riche, Chris Dawe, Jagoda Korbelik, Stephen Lam, "Quantitative architectural analysis of bronchial intraepithelial neoplasia," Proc. SPIE 3921, Optical Diagnostics of Living Cells III, (27 Apr. 2000); https://doi.org/10.1117/12.384231 and Guillaud et al. Cellular Oncology 26 (2004) 31-43.

U.S. Published Application No. 20090292027A1 to Ruvolo et al. discloses that cosmetic products can target keratinocyte organization.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIGS. 3a-3c show images of skin.

FIG. 5 sets out parameters for filters used in image processing.

DETAILED DESCRIPTION OF DISCLOSED EMBODIMENTS

Definitions

"Architecture" or "cell architecture" as used herein means the structure and form of a living cell, specifically the structure of a tissue considered in terms of the form and spatial relations of its constituent cells.

"Arrangement" or "cell arrangement" as used herein means the manner in which particular cell types cling together often giving them distinct arrangements.

"Artificial intelligence" as used herein broadly describes any computationally intelligent systems that combine knowledge, techniques, and methodologies. An AI engine may be any system configured to apply knowledge and that can adapt itself and learn to do better in changing environments. Thus, the AI engine may employ any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing. Employing any computationally intelligent techniques, the AI engine may learn to adapt to unknown and/or changing environment for better performance.

The term "capturing (an image)", or any form thereof, refers to the use of an image capture device to acquire an image. "Capturing" may refer to the direct act of using the image capture device to acquire the image. It may also include indirect acts to promote acquisition. To this end, "capturing" may include the indirect acts of providing access to hardware, or to at least one of a client-based algorithm and a server-based algorithm for causing the image capture device to capture an image. This may be accomplished by providing a user with software to aid in the image capture process or providing the user with access to a network location at which the software resides. Also consistent with certain embodiments of the invention, capturing may include at least one of receiving an instruction from the subject to capture an image, indicating to the subject before the image is captured, and indicating to the subject when the image is captured.

"Cell organization" as used herein means the components that make up the cell and how they are arranged inside it.

"Epidermal tissue structure" as used herein includes keratinocytes at each distinct stage of differentiation; melanocytes; Langerhans cells; resident T lymphocytes and Merkel cells. "Epidermal tissue structure" includes cell organization, topology, geometry, arrangement, and architecture as these terms are defined herein. "Epidermal tissue structure" is a subset of "epithelial tissue structure."

"Epidermis" as used herein means the outer layer of skin, and is divided into five strata, which include the: stratum corneum, stratum lucidum, stratum granulosum, stratum spinosum, and stratum basale. The stratum corneum contains many layers of dead, anucleated keratinocytes that are essentially filled with keratin. The outermost layers of the stratum corneum are constantly shed, even in healthy skin. The stratum lucidum contains two to three layers of anucleated cells. The stratum granulosum contains two to four layers of cells that are held together by desmosomes that contain keratohyaline granules. The stratum spinosum contains eight to ten layers of modestly active dividing cells that are also held together by desmosomes. The stratum basale contains a single layer of columnar cells that actively divide by mitosis and provide the cells that are destined to migrate through the upper epidermal layers to the stratum corneum. The predominant cell type of the epidermis is the keratinocyte. These cells are formed in the basal layer and exist through the epidermal strata to the granular layer at which they transform into the cells know as corneocytes or squames that form the stratum corneum. During this transformation process, the nucleus is digested, the cytoplasm disappears, the lipids are released into the intercellular space, keratin intermediate filaments aggregate to form microfibrils, and the cell membrane is replaced by a cell envelope made of cross-linked protein with lipids covalently attached to its surface. Keratins are the major structural proteins of the stratum corneum. Corneocytes regularly slough off (a process known as desquamation) to complete an overall process that takes about a month in healthy human skin. In stratum corneum that is desquamating at its normal rate, corneocytes persist in the stratum corneum for approximately 2 weeks before being shed into the environment.

"Epithelial tissue structure" as used herein includes any of the cells making up an epithelium at each distinct stage of differentiation. "Epithelial tissue structure" includes cell organization, topology, geometry, arrangement and architecture as these terms are defined herein.

"Epithelium" as used herein means a thin, continuous, protective layer of cells that line the outer surfaces of organs and blood vessels throughout the body, as well as the inner surfaces of cavities in many internal organs. It is classified based on the number of layers that make up the tissue: simple, stratified, and pseudostratified. It may also be classified histologically, according to the cell shape: squamous, columnar, and cuboidal. It is primarily involved in providing protection of the underlying structures, secretory functions, transcellular transport, and selective absorption. Examples of epithelium include the epidermis; the lining of the digestive tract; and the lining of the reproductive tract.

"Geometry" or "cell geometry" as used herein means the characteristic positioning of organelles within the cell body in order for a cell to be able to carry out its specified function.

The term "image capture device", similar terms, and terms representing structures with similar functions may include one or more of a digital camera, webcam, film camera, analog camera, digital video camera, scanner, facsimile machine, copy machine, infrared imager, (laser scanning) confocal reflectance microscope, confocal fluorescence microscope, optical coherence tomography (OCT), multiphoton fluorescence (MPF) microscope, second harmonic generation (SHG) microscope, fluorescence lifetime imaging microscope (FLIM), photo acoustic microscope or any other mechanism for acquiring an image of a subject's skin. An ultrasonic device might provide skin thickness information, or it might create a map on an area of the external location. Thus, the term "image" as used herein may be broader than a picture. Combinations of image capture devices may be used. For example, an image captured on photographic paper using a film camera might then be scanned on a flat bed scanner to create another image. A confocal endoscope that is compatible with the biopsy channel of a conventional endoscope can be used to capture images of epithelial cells in a method according to the invention. See, e.g., Jiafu Wang, Min Yang, Li Yang, Yun Zhang, Jing Yuan, Qian Liu, Xiaohua Hou, Ling Fu, A Confocal Endoscope for Cellular Imaging, Engineering, Volume 1, Issue 3, 2015, Pages 351-360, ISSN 2095-8099, https://doi.org/10.15302/J-ENG-2015081. (https://www-.sciencedirect.com/science/article/pii/S2095809916300121).

The term "image processing technique" or similar terms, may include a software program, computer, application specific integrated circuit, electronic device and/or a processor designed to identify in an image one or more characteristics, such as a skin condition. Such techniques may involve binarization, image partitioning, Fourier transforms, fast Fourier transforms (FFTs), and/or discrete cosine transforms may be performed on all or part of the image, resulting in coefficients. Based on the coefficients, conditions may be located, as known in the art. Artificial intelligence, such as fuzzy logic, neural networks, genetic programming and decision tree programming, may also be used to identify conditions. Alternatively, one or more digital filters may be passed through the image for locating specific conditions. These examples are provided for illustrative purposes with the understanding that any image processing technique may be used.

"Morphological Snakes" are a family of methods for image segmentation. Their behavior is similar to that of active contours (for example, Geodesic Active Contours or Active Contours without Edges). However, Morphological Snakes use morphological operators (such as dilation or erosion) over a binary array instead of solving partial differential equations over a floating-point array, which is the standard approach for active contours. This makes Morphological Snakes faster and numerically more stable than their traditional counterpart. (P. Márquez-Neila, L. Baumela and L. Alvarez, "A Morphological Approach to Curvature-Based Evolution of Curves and Surfaces," in IEEE Transactions on Pattern Analysis and Machine Intelligence, vol. 36, no. 1, pp. 2-17, January 2014, doi: 10.1109/TPAMI.2013.106).

"Topology" or "cell topology" as used herein means the connectivity among cells in a tissue.

"Marker controlled Watershed segmentation" is a region-based technique that utilizes image morphology. (Jadwiga Rogowska, in Handbook of Medical Imaging, 2000). It requires selection of at least one marker ("seed" point) interior to each object of the image, including the background as a separate object. The markers are chosen by an operator or are provided by an automatic procedure that takes into account the application-specific knowledge of the objects. Once the objects are marked, they can be grown using a morphological watershed transformation.

In the following detailed description, reference is made to the accompanying drawings which form a part hereof, and in which are shown by way of illustration embodiments that may be practiced. It is to be understood that other embodiments may be utilized, and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

In various embodiments, methods, apparatuses, and systems for non-invasive or minimally invasive assessment of epithelial tissue structure are provided. In exemplary embodiments, a computing device may be endowed with one or more components of the disclosed apparatuses and/or systems and may be employed to perform one or more methods as disclosed herein.

Visualization of cells in skin, such as for the detection of cancer, normally requires invasive biopsy and review by a trained pathologist who assesses the size, shape, and distribution of epidermal tissue and identifies patterns typical of healthy skin or of skin cancer. However, embodiments herein provide methods for non-invasive assessment of epidermal tissue structure. Digital images and processing of grey-level intensities are used to identify cells. As an example, in a confocal reflectance image, keratinocytes appear to have a bright border, which consists of high gray-levels, while the cytoplasm and intercellular spaces appear as a dark center, which consists of low gray-level intensities. More specifically, embodiments provide an automated algorithm that may be used to identify epidermal tissue structure, and/or to specify the coordinates/locations of cells in the epidermal tissue structure, through non-invasive confocal imaging or other types of imaging, such as OCT, MPF, SHG, FLIM, etc. as mentioned above. Methods herein may be repeated to analyze other areas of tissue.

In accordance with an embodiment, a method for characterizing epithelial tissue structure includes comparing, by one or more computing devices, an unknown image segment to a known epithelial tissue structure model image segment to determine the degree of match between the unknown segment and the known segment; comparing, by the one or more computing device, the determined degree of match to a predetermined value, and characterizing, by the one or more computing device, the particular segment of the sample as a epithelial tissue structure if the determined degree of match is sufficient, such as equal to or above the predetermined value. The degree of match may be determined by any suitable method/calculation to determine the degree of similarity. The degree of match may include symmetry measurements and mathematical operations such as subtraction, division and multiplication of the known segment and the unknown image segment.

In an embodiment, the predetermined value may be a range or a single value.

For example, a method is provided in which the difference between a particular segment of an image and a known epithelial tissue structure model image segment is examined. A comparative analysis may also be used to determine that an image does not depict an epithelial tissue structure.

Thus, in an embodiment, there is provided a method for characterizing epithelial tissue structure, comprising comparing, by one or more computing device, an unknown image segment to a known epithelial tissue structure model image segment to determine a difference value between the particular segment of the diagnostic image and a value derived from a known epithelial tissue structure model image segment; comparing, by one or more computing device, the determined difference to a predetermined threshold; and characterizing, by one or more computing device, the particular segment of the sample as an epithelial tissue structure if the determined difference is equal to or below the predetermined threshold.

In embodiments, the unknown image segment may be n-dimensional, such as a 3-dimensional image of a cell volume within a tissue volume or a 4-dimensional image of an epidermal tissue structure maturing as it migrates and changes shape and volume from the basal layer to the stratum corneum. The unknown image segment may be (a) a line sampled through a living cell (1D), (b) on a plane (2D) bisecting a living cell center (1D function) where the 1D function is rotated in an en face plane about the cell center, (c) a volume (3D) where directional cell aspects are defined, or (d) a movie (4D) digitally sampled and analyzed over a life cycle under cellular maturation.

As used herein, the term "en face" refers to a 2-dimensional image of a plane parallel to the surface of the tissue.

In an embodiment, the unknown image segment may be acquired by non-invasive or minimally invasive imaging with cellular resolution. Examples of suitable non-invasive or minimally invasive imaging methods include confocal microscopy, optical coherence tomography, photo-thermal microscopy, etc.

Image masking is a process of graphics software used to hide some portions and to reveal other portions of an image. It is a non-destructive process of image editing. Most of the time it enables a user to adjust and tweak the mask later if necessary. Very often, it is an efficient and more creative way of image manipulation.

As used herein with respect to image processing, a "mask" is a term for a model image segment (such as the epithelial tissue structure model) from which similar regions are to be searched in an unknown image segment.

This method may be used to non-invasively evaluate epidermal tissue structure populations as a quantitative morphometric diagnostic in skin condition detection and in evaluation of dermatological cosmetics. Methods herein may be used as a secondary test in conjunction with, or as a follow-on to, other detection methods.

Example

Reflectance confocal microscopy (RCM) allows in vivo visualization of epithelial tissue structure at a cellular level. The study of RCM images provides information on the topological and geometrical properties of the epidermis. These properties change in each layer of the epidermis and with age.

Studying RCM requires manual identification of each cell to derive geometrical information, which is then used to compare populations, presenting physiological or biological differences. This task is time-consuming and subject to human error, highlighting the need for an automated cell identification method.

Step 1

The first step is to differentiate between the tissue area and the dark background. This can be done by applying an appropriate band-width filter on the Fourier-transformed image.

In mathematics, a Fourier transform (FT) is a mathematical transform that decomposes functions depending on space or time into functions depending on spatial or temporal frequency. The term Fourier transform refers to both the frequency domain representation and the mathematical operation that associates the frequency domain representation to a function of space or time. Almost every imaginable signal can be broken down into a combination of simple waves. An image is a "two dimensional" signal. The Fourier Transform is an important image processing tool which is used to decompose an image into its sine and cosine components. The Fourier Transform is used in a wide range of applications, such as image analysis, image filtering, image reconstruction and image compression. Wang et al. discloses the use of FT to detect collagen fiber orientation in the dermis. Wang et al. "Age-related morphological changes of the dermal matrix in human skin documented in vivo by multiphoton microscopy" J. Biomed. Opt. 23(3), 030501 2018.

Tissue areas can sometimes contain background enclosures, which can be identified using the Morphological Geodesic Active Contour (MGAC) or "Snake" method. The combination of the Fourier Transform method and the Snake method leads to a more accurate identification of borders between tissue and background.

Step 2 The second step is to identify individual cells in the segmented tissue area. To perform this task, the following methods were tested: A) Gabor filtering, which analyzes local textural aspects in the tissue and highlights cell membranes; B) Frangi filtering, which detects vessel-like structures, modified to detect blobs, that in this case represent keratinocytes; and C) Sato filtering, which detects curvilinear structures in images. A combination of methods could be employed in accordance with the invention.

Gabor filter is a linear filter used for texture analysis, that analyzes whether there is any specific frequency content in the image in specific directions in a localized region around the point or region of analysis. See, e.g., J. Kamarainen, "Gabor features in image analysis," 2012 3rd International Conference on Image Processing Theory, Tools and Applications (IPTA), 2012, pp. 13-14, doi: 10.1109/IPTA.2012.6469502.

Frangi et al., Multiscale Vessel Enhancement Filtering, Lecture Notes in Computer Science February 2000, discloses a method for vessel enhancement filtering which is based on local structure.

Sato et al., Three-dimensional multi-scale line filter for segmentation and visualization of curvilinear structures in medical images, Medical Image Analysis (1998) volume 2, number 2, pp 143-168, discloses a method for the enhancement of curvilinear structures such as vessels and bronchi in three-dimensional (3-D) medical images.

Step 3

The outputs of the methods are then locally normalized and binarized, and small elements are removed using connected-component analysis. The output is then skeletonized, and the obtained skeletons (representing cell membranes) are cleaned by pruning and removing spurious branches and loops using a sequential repeated dilation followed by skeletonization steps (preferably two).

A distance transform is then applied on the skeletons and local maxima are identified, representing cell centers, which are then used to apply a marker-controlled watershed algorithm. This step considers the original image as a topographic surface, flooded starting from the seeds. The frontiers between flooded areas define the cell borders.

The results from the methods were compared against manual cell identification on sample images and on artificially created test images. The results show that automatically identifying cells can be achieved. With this respect, the Gabor filtering method appears to be better in identifying keratinocytes of the granular layer, whereas the Frangi filtering works better for the spinous layer. The Sato filter worked best in identifying spinous cells and it is expected that the Gabor filter followed by the Sato filter will work best for granular cells.

This is a promising step towards automatic cell identification and characterization of tissue geometry.

Although the algorithms have been applied to Reflectance Confocal Microscopy (RCM), they could be applied to other imaging technologies including, e.g., optical coherence tomography (OCT) and Line-field Optical Coherence Tomography, MPF, SHG, FLIM, photoacoustic microscopy, MRI, etc. and in general to image modalities with resolution capable of providing information at the cell level and the organization of epithelial organization.

Although the algorithms are used on skin epidermis, they could be used for any type of epithelial tissue, including, e.g., gut, lung, mouth.

In accordance with the invention, a method of cell identification includes the following steps:
- segmenting images to remove non-cellular areas;
- combining Fourier filtered image for external contours with Morphological Snakes image for cellular areas;
- identifying regions of interest;
- wherein identifying includes local normalizing outputs and turning resultant images into gray scale;
- identifying individual cells within the tissue, wherein parameter employed for identification depends upon layer of interest;
- wherein Gabor filter is employed on Fourier filtered image based on white ridges detection;
- wherein Frangi filter is employed on negative of Fourier filtered image based on white ridges detection;
- wherein modified Frangi filter is employed based on black blobs detection; and wherein Sato filter is employed on original image background set to 0.

In accordance with the invention, a method of cell identification includes the following steps:
normalization;
set background to 0 level;
binarization;
connected component analysis to remove noise.

In accordance with the invention, a method of cell identification includes the following steps:
identify cells' centers (for each method in step 2, with or without step 3.4);
clean the results of the previous step (for each method);
local normalization;
binarization;
connected components analysis to remove noise (or signals coming from intracellular structures);
distance transform on clean binary image;
local maxima (considered as the cell center);
remove overlapping cell centers, centers that are too close to the tissue border, cell centers within the background, cell centers within the membrane.

In accordance with the invention, a method of cell identification includes the following steps:
rebuild the cells;
marker controlled watershed from these centers/Voronoi;
evaluate accuracy with DAccuracy by comparing real vs. detected cells. The DAccuracy software allows to compute some accuracy measures of an N-dimensional detection or segmentation image when the ground-truth is represented by a CSV file or an image. It works in 3 contexts: one-to-one: single ground-truth, single segmentation; one-to-many: unique ground-truth, several segmentations (typically obtained with several methods); many-to-many: set of ground-truth/segmentation pairs. DAccuracy is available at https://gitlab.inria.fr/edebreuv/daccuracy.

In accordance with the invention, a method of cell identification includes the following steps:
extraction of characteristics and classification:
define descriptors characteristic of the different structures of the epidermis and compute them for all images and compare results per layer/participant/condition;
preprocessing to improve contrast between cells (Fourier filtering);
Gabor filter;
Frangi filter;
Sato filter;
evaluate accuracy (DAccuracy workflow).

In accordance with the invention, a method of cell identification is employed to obtain a model of the evolution of the skin between early age and adulthood.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A non-invasive or minimally invasive method for characterizing epithelial tissue structure, comprising:
identifying cell coordinates information in an unknown image segment, wherein the unknown image segment is a Reflectance Confocal Microscopy image and comprises tissue area and dark background, and wherein identifying the cell coordinates information comprises:
performing, on the unknown image segment, image processing to differentiate between the tissue area and the dark ground; and
identifying individual cells in the tissue area by producing a further filtered unknown image segment;
determining a degree of match between the further filtered unknown image segment and a known epithelial tissue structure model image segment by comparing, by one or more computing devices, the segmented cellular areas in the further filtered unknown image segment to cellular areas in the known epithelial tissue structure model image segment, wherein determining the degree of match further comprises determining a difference value relative to a derived value from the known epithelial tissue structure model image segment;
comparing, by the one or more computing devices, the determined degree of match to a predetermined value; and
characterizing, by the one or more computing devices, the further filtered unknown image segment as an epithelial tissue structure based on the comparison of the determined degree of match to the predetermined value indicating the determined difference value is equal to or below a predetermined threshold.

2. The method of claim 1, further comprising:
identifying, by an algorithm, cell coordinates information; and
extracting, using the identified cell coordinates information, values of epithelial tissue structure parameters.

3. The method of claim 2, further comprising extracting, using the identified epithelial cell coordinates information, values of cell geometry and cell topology parameters.

4. The method of claim 3, wherein the parameters are selected from cell area, perimeter, cell density, distribution of nearest neighbors, and distributions of distances between neighbors.

5. The method of claim 4, further comprising comparing, using the parameters, images for screening for an appropriate treatment selected from use of ingredients and use of formulations.

6. The method of claim 3, wherein at least one of the unknown image segment or the known epithelial tissue structure model image segment is a movie taken during maturation.

7. The method of claim 1, wherein the unknown image segment is acquired by non-invasive or minimally invasive imaging with cellular resolution.

8. The method of claim 7, wherein the non-invasive or minimally invasive imaging is selected from the group consisting of reflectance confocal microscopy, fluorescence confocal microscopy, fluorescence lifetime microscopy, multiphoton fluorescence microscopy, second harmonic generation microscopy, chemiluminescence imaging, photoacoustic microscopy, magnetic resonance imaging, optical coherence tomography, line-field optical coherence tomography and photo-thermal microscopy.

9. The method of claim 1, further comprising, based on the determined difference being above the predetermined threshold, characterizing the particular segment of the sample as not an epithelial tissue structure skin cell.

10. The method of claim 1, further comprising characterizing a training set of epithelial tissue structure to be used for screening for appropriate treatment selected from use of ingredients and use of formulations.

11. The method of claim 1, further comprising identifying cell types in the unknown image segment, the identified cell types comprising keratinocytes, melanocytes, Langerhans cells, resident T lymphocytes and Merkel cells,
wherein the filtering to identify individual cells in the tissue area further comprises utilizing one or more of a Gabor filter, a Frangi filter, or a Sato filter.

12. The method of claim 11, wherein:
the input to the Gabor filter is the Fourier-filtered unknown image segment,
the input to the Frangi filter is at least one of the Fourier-filtered unknown image segment or a negative of the Fourier-filtered unknown image segment, and
the input to the Sato filter is the unknown image segment.

13. One or more non-transitory computer readable medium storing instructions that, when executed by a processor, cause the processor to:
identify cell coordinates information in an unknown image segment, wherein the unknown image segment is a Reflectance Confocal Microscopy image and comprises tissue area and dark background, and wherein identifying the cell coordinates information comprises:
perform, on the unknown image segment, image processing to differentiate between the tissue area and the dark ground; and
identify individual cells in the tissue area by producing a further filtered unknown image segment;
determine a degree of match between the further filtered unknown image segment and a known epithelial tissue structure model image segment by comparing, by one or more computing devices, the further filtered unknown image segment to the known epithelial tissue structure model image segment, wherein determining the degree of match further comprises determining a difference value relative to a derived value from the known epithelial tissue structure model image segment;
compare the determined degree of match to a predetermined value; and
characterize the further filtered unknown image segment as an epithelial tissue structure based on the comparison of the determined degree of match to the predetermined value indicating the determined difference value is equal to or below a predetermined threshold.

\* \* \* \* \*